United States Patent [19]

Whitt

[11] Patent Number: 5,331,160

[45] Date of Patent: Jul. 19, 1994

[54] PARTICLE-BEAM GENERATOR FOR LC/MS INTERFACE

[75] Inventor: Robert T. Whitt, Carrollton, Tex.

[73] Assignee: Hewlett-Packard Company, Palo Alto, Calif.

[21] Appl. No.: 40,712

[22] Filed: Mar. 31, 1993

[51] Int. Cl.[5] .......................... B01D 59/44; H01J 49/00
[52] U.S. Cl. ....................................... 250/288; 250/282
[58] Field of Search .................. 250/282, 288, 288 A, 250/423 R

[56] References Cited

U.S. PATENT DOCUMENTS

| | | | |
|---|---|---|---|
| 4,629,478 | 12/1986 | Browner et al. | 250/288 A |
| 4,801,430 | 1/1989 | Albert et al. | 250/288 A |
| 4,814,612 | 3/1989 | Vestal et al. | 250/282 |
| 4,980,057 | 12/1990 | Dorn et al. | 250/288 A |
| 4,982,097 | 1/1991 | Slivon et al. | 250/282 |
| 5,024,952 | 6/1991 | Alsop | 436/177 |
| 5,162,650 | 11/1992 | Bier | 250/282 |

OTHER PUBLICATIONS

Apffel, Alex, "Environmental Applications of Magic LC/MS", *Proceedings of the Third Annual United States Environmental Protection Agency Symposium on Solid Waste Testing and Quality Assurance*, vol. II, Jul. 1987, Washington, D.C., pp. 6-119-6-136.

Willoughby, Ross C. and Richard F. Browner, "Monodisperse Aerosol Generation Interface for Combining Liquid Chromatography with Mass Spectroscopy", *Analytical Chemistry*, vol. 56, No. 14, Dec. 1984, pp. 2226-2631.

"Presenting the MS Engine", Publication No. 23-59-53-4760 by Hewlett-Packard Company, Apr. 1990.

"HP Particle Beam LC/MS . . . It Makes LC/MS as Practical as GC/MS", Publication No. 23-5956-4133 by Hewlett-Packard Company, Jun. 1988.

*Primary Examiner*—Bruce C. Anderson

[57] ABSTRACT

An LC/MS (liquid chromatography and mass spectrometry) system includes a particle-beam generator that handles aqueous inputs with enhanced efficiency. Helium from a helium source is passed through organic liquid in a bubbler. The organic liquid is maintained at about 4° C. The resulting mixture of helium and organic vapor is used as a dispersant gas by the particle-beam generator. The dispersant gas contacts a predominantly aqueous liquid chromatography effluent before a nebulizer causes the effluent to break up into droplets. The solvent in the droplets is vaporized in a desolvation chamber. A momentum separator removes helium, organic vapor, and solvent vapor from an analyte particle beam. The analyte particle beam is directed to a mass spectrometer for identification and quantification. This LC/MS has demonstrated an improvement in signal strength of up to an order of magnitude relative to a similar LC/MS without the organic vapor in the dispersant gas.

10 Claims, 2 Drawing Sheets

PARTICLE-BEAM GENERATOR FOR LC/MS INTERFACE

BACKGROUND OF THE INVENTION

The present invention relates to analytical chemistry and, more particularly, to a particle-beam generator, for example, to an interface between a liquid chromatography system and a mass spectrometer. A major objective of the present invention is to provide for more effective nebulization of liquid chromatography effluent having a high aqueous content.

LC/MS systems, which combine liquid chromatography (LC) and mass spectrometry (MS), are used for several purposes including 1) environmental studies, for example, to evaluate water, soil and waste; 2) food analysis, to identify contaminants and adulterants; 3) pharmaceutical development, to analyze natural and synthetic products; and 4) life sciences, to characterize protein components.

Liquid chromatography is a method of separating components of a sample mixture. At any given time during separation, some molecules of a component are adsorbed to a stationary solid support, while other molecules are dissolved in a liquid solvent flowing past the solid support. The adsorbed molecules are said to be in a "stationary phase" while the dissolved molecules are said to be in a "mobile phase". Sample components can differ significantly in their solubility in a given solvent. Specifically, nonpolar components tend to dissolve more readily in organic solvents, while polar components tend to dissolve more readily in water. To accommodate samples with both polar and nonpolar component, reverse-phase gradient-elution liquid chromatography (GELC) provides for a gradual transition of organic solvent to water as the liquid solvent in an LC system.

At equilibrium, the rate at which a component's molecules in the stationary phase are released to the mobile phase equals the rate at which the same component's molecules in the mobile phase are adsorbed to the stationary phase. For each component, the ratio of the number of molecules in the stationary phase to the number of molecules in the mobile phase is quantified by a partitioning coefficient. This partitioning coefficient thus corresponds to the average percentage of time the molecules of a component are in the mobile phase. This percentage correlates with the mobility of the component past the solid support. Sample components with different mobilities separate, as they progress past the solid support. With sufficient separation, the components emerge serially in the chromatography effluent.

To complete the analysis of a sample mixture, the eluting components need to be identified and quantified. Various types of detectors, for example, ultra-violet absorption detectors positioned to monitor the ultraviolet absorption characteristics of the effluent, can be used to detect eluting components. Since each component has a characteristic retention time in a chromatographic column, the time of detection is often used for component identification, while the degree of ultraviolet absorption can be used to quantify the component.

However, it is often not possible to identify and quantify sample components dissolved in the chromatography effluent. Some components are not readily detectable, others appear in quantities too small to measure reliably, and others can not be uniquely identified by their retention times. In these situations, and others, a mass spectrometer can be used for sample component identification and quantification.

A mass spectrometer provides a mass spectrum of a sample component by separating sample subcomponents according to molecular mass and quantifying the number of subcomponent molecules at molecular mass. (The samples input to the mass spectrometer are the serialized components of the sample input from the LC system.) Mass spectrometers typically operate by ionizing sample molecules and then sweep-filtering the resulting ions according to their charge-to-mass ratios. To minimize interference with ion movement through the mass filter, mass spectrometers are operated under vacuum conditions.

The liquid output of the LC system is not directly compatible with the requirements for ionization and the vacuum conditions of the mass spectrometer. Accordingly, LC/MS interfaces can include a particle-beam generator that converts a liquid flow into a particle beam. A typical particle-beam generator comprises a nebulizer, a desolvation chamber, a momentum separator, and a transfer probe. In the nebulizer, the LC effluent is joined by a stream of helium and converted into an aerosol of uniform droplets. Solvent is vaporized as the droplets traverse the desolvation chamber, freeing sample particles.

The sample particles proceed as a beam through a momentum separator. Vacuum pumps maintain the momentum separator at a lower pressure than the desolvation chamber. The vacuum pumps divert throughgoing particles laterally, drawing lower momentum helium and solvent vapor into the vacuum exhaust system. The higher momentum sample particles are deflected less and are thus permitted to enter the transfer probe. Particles entering the transfer probe are directed to the ion source of the mass spectrometer.

The efficiency of such a particle-beam generator depends, in part, on the solvent of the liquid input. The particle-beam generator is most effective when the solvent is primarily organic, and less efficient when the solvent is primarily aqueous. The mass spectrometer signal strength can fall by 70% or more when the solvent is more than 50% aqueous. This signal loss is particularly problematic in GELC since it makes it difficult to compare mass spectra from earlier eluting components with those of later eluting samples.

This problem has been addressed by adding organic solvent to an aqueous LC effluent. However, this approach results in unacceptable band broadening. What is needed is a system that efficiently generates a particle beam from an aqueous input without unacceptable band broadening.

SUMMARY OF THE INVENTION

In accordance with the present invention, a particle-beam generator includes a carrier gas source, a means for mixing the carrier gas with an organic vapor, a nebulizer, a desolvation chamber, and a momentum separator. The carrier gas and organic vapor mixture, "dispersant gas" herein, contacts a solution of an analyte in a solvent. The solution can be the effluent of a LC, preferably a GELC, system. Contact between the dispersant gas and solution preferably initiates before the nebulizer causes the solution to break up into droplets. The desolvation chamber provides for removal of solvent from the droplets, rendering an analyte particle beam. The momentum separator removes carrier gas, organic vapor and solvent vapor from the particle beam. The particle beam can then be directed to a mass spectrometer for identification and quantification.

A bubbler can be used for mixing the carrier gas with an organic solvent. The bubbler can contain an organic liquid such as hexane, methanol and acetonitrile. Preferably, temperature control means, such as a bath of ice water, can be used to maintain the temperature of the organic liquid below 20° C.; optimal results have been attained between 0° C. and 8° C. The carrier gas, for example helium, can be bubbled through the organic liquid. The path of the helium bubbles in the bubbler can be made long enough for an equilibrium to be established between the organic vapor pressure in the bubbles and the organic liquid so that the dispersant gas exiting the bubbler is at least 90% saturated with organic vapor.

The organic vapor should be soluble in the LC solvent. Where the LC solvent is predominantly water, the organic vapor should be soluble in water. Generally, organic liquids suitable for gradient elution with water are suitable sources of the organic vapor. For example, acetonitrile, isopropyl alcohol, tetrahydrofuran (THF), and, to a lesser extent, dimethyl formamide are suitable organic vapors when the LC solvent is predominantly aqueous.

An LC/MS system in accordance with the invention includes the particle-beam generator as part of the LC/MS interface. The output of the gradient-elution liquid-chromatography system is converted to a particle beam by the particle-beam generator. The resulting particle beam is directed to the mass spectrometer.

Including organic solvent vapor with the carrier gas results in improved signal strength from a sample in an aqueous liquid. The improvements are most pronounced when temperatures are lowered to the specified ranges. For example, signal strength increases by an order of magnitude when the bubbler bath temperature is dropped from room temperature to about 4° C. In the context of a gradient-elution LC/MS system, the present invention provides for enhanced and more comparable readings for samples with analytes having a wide range of polarities. These and other features and advantages of the present invention are apparent from the description below with reference to the following drawings.

DESCRIPTION OF THE PREFERRED EMBODIMENTS

Figure 1:
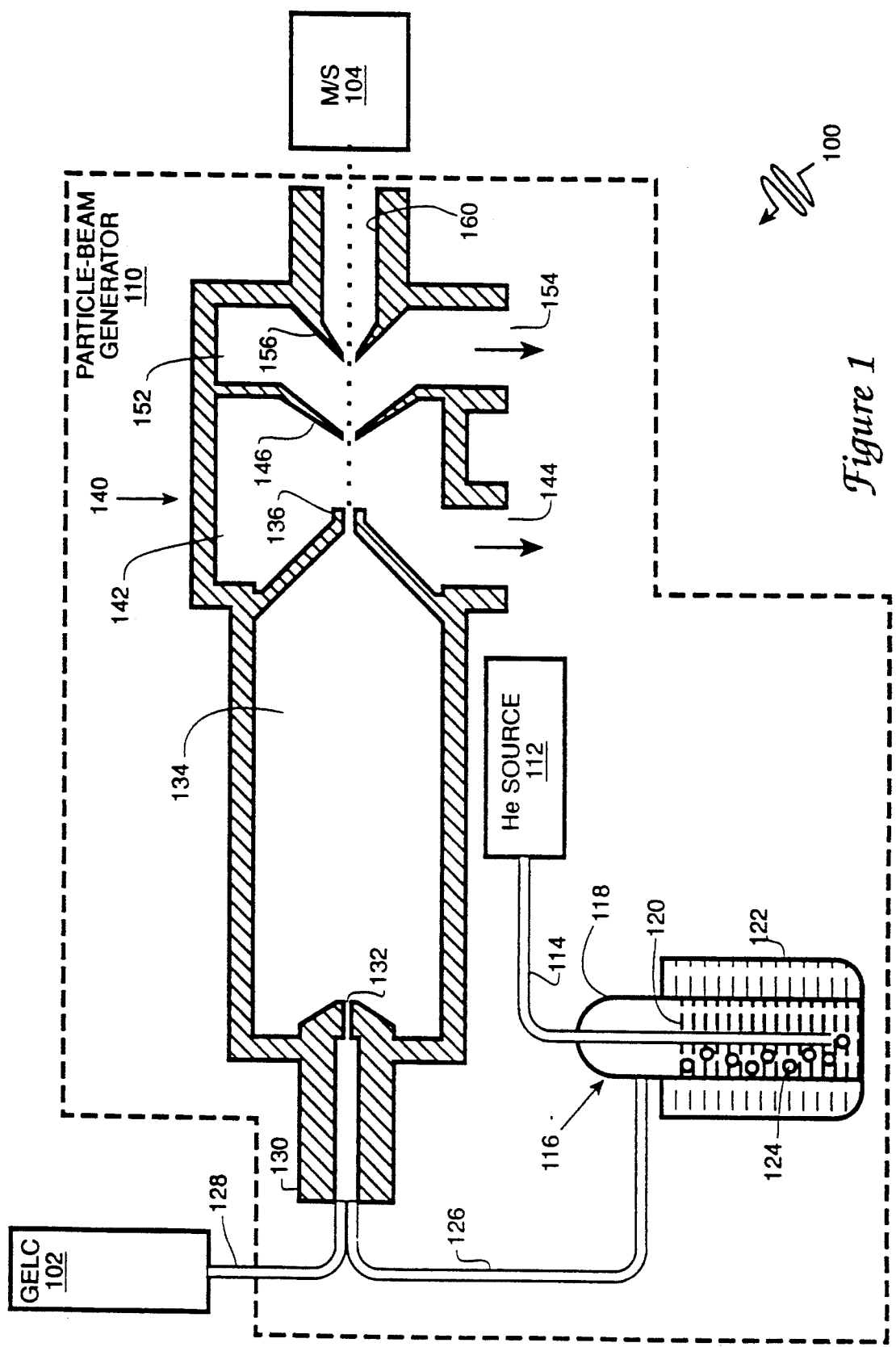
FIG. 1 is a schematic view of an LC/MS system incorporating a particle-beam generator in accordance with the present invention.

An LC/MS system 100 comprises a gradient-elution liquid-chromatography system 102, a mass spectrometer 104, and a particle-beam generator 110, as illustrated in FIG. 1. Gradient-elution liquid-chromatography (GELC) system 102 separates component analytes of a sample mixture. Each analyte emerges from liquid-chromatography system 102 dissolved in a solvent. When gradient-elution liquid-chromatography system 102 is operated in reverse phase gradient mode, components emerging last are dissolved in a predominantly aqueous solvent. Particle-beam generator 110 removes the solvent and provides a beam of analyte particles to the ionization source of mass spectrometer 104. For each component analyte, mass spectrometer 104 provides a mass spectrum permitting reliable identification and quantification.

Particle-beam generator 110 includes a carrier-gas source 112 which provides a stream of helium (He) under pressure through a conduit 114 to a bubbler 116. Bubbler 116 includes an enclosed bubble chamber 118 filled with a volatile organic liquid 120, such as acetonitrile. Conduit 114 extends downward well into organic liquid 120 so that the exiting helium must rise through organic liquid 120 before exiting chamber 118.

The temperature of organic liquid 120 is controlled by temperature controller 122. Temperature controller 122 is a bath of ice water that maintains organic liquid at 4° C. Alternatively, temperature controller can include a circulating coolant maintained at a selected temperature below 20° C. Preferably, the selected temperature is between 0° C. and 8° C. to optimize the effects of bubbler 116 on the carrier gas.

Helium forms into bubbles 124 that rise through organic liquid 120. Organic liquid 120 vaporizes where it interfaces bubbles 124, which thus acquire an organic content. Bubbler 116 is dimensioned so that the dispersant gas exiting chamber 118 is substantially saturated with organic vapor.

The dispersant gas is conveyed to a particle-beam generator 110 along conduit 126. Concurrently, effluent from liquid chromatography system 102 is conveyed to particle-beam generator 110 via a conduit 128. The effluent and dispersant gas contact each other within a nebulizer 130 of particle-beam generator 110. The dispersant gas and the effluent flow through a nozzle 132 of nebulizer 130, so that an aerosol of droplets having a narrow range of diameters enters a desolvation chamber 134 of particle-beam generator 110.

Desolvation chamber 134 is held at close to ambient temperature and pressure. The solvent in the aerosol droplets is vaporized as they transverse desolvation chamber 134 toward its exit jet nozzle 136. What exits nozzle 136 is a mixture of helium, organic vapor, mobile phase vapor, and analyte particles.

The mixture accelerators toward a lower-pressure momentum separator 140 of particle-beam generator 110. A first stage 142 of momentum separator 140 is maintained at a pressure of about 2-10 torr. Upon entering a first stage 142 of momentum separator 140, the mixture is focused into a beam which expands at supersonic speed. The helium, organic vapor and solvent vapor are diverted by a vacuum into a first exhaust 144. The relatively massive analyte particles pass through a central bore in a first stage skimmer 146.

A second stage 152 of momentum separator 140 operates in a similar manner to evacuate the traces of helium, organic vapor and solvent vapor not exhausted by first stage 142. Second stage 152 includes a second-stage exhaust 154 and a second-stage skimmer 156. The vacuum implementing second-stage exhaust 154 maintains a second-stage pressure below 1 torr.

The analyte particle beam exiting through an aperture of second-stage skimmer 154 enters an output bore 160 of particle-beam generator 110. From bore 160, the particle beam is directed through a transfer probe (not shown) and enters an ion source of mass spectrometer 104. The ion source operates at a pressure of about $10^{-4}$ torr. The ion source ionizes the particles so that they can be filtered by a quadrupole of the mass spectrometer. Particles passing through the quadrupole are detected and quantified by mass.

Figure 2:
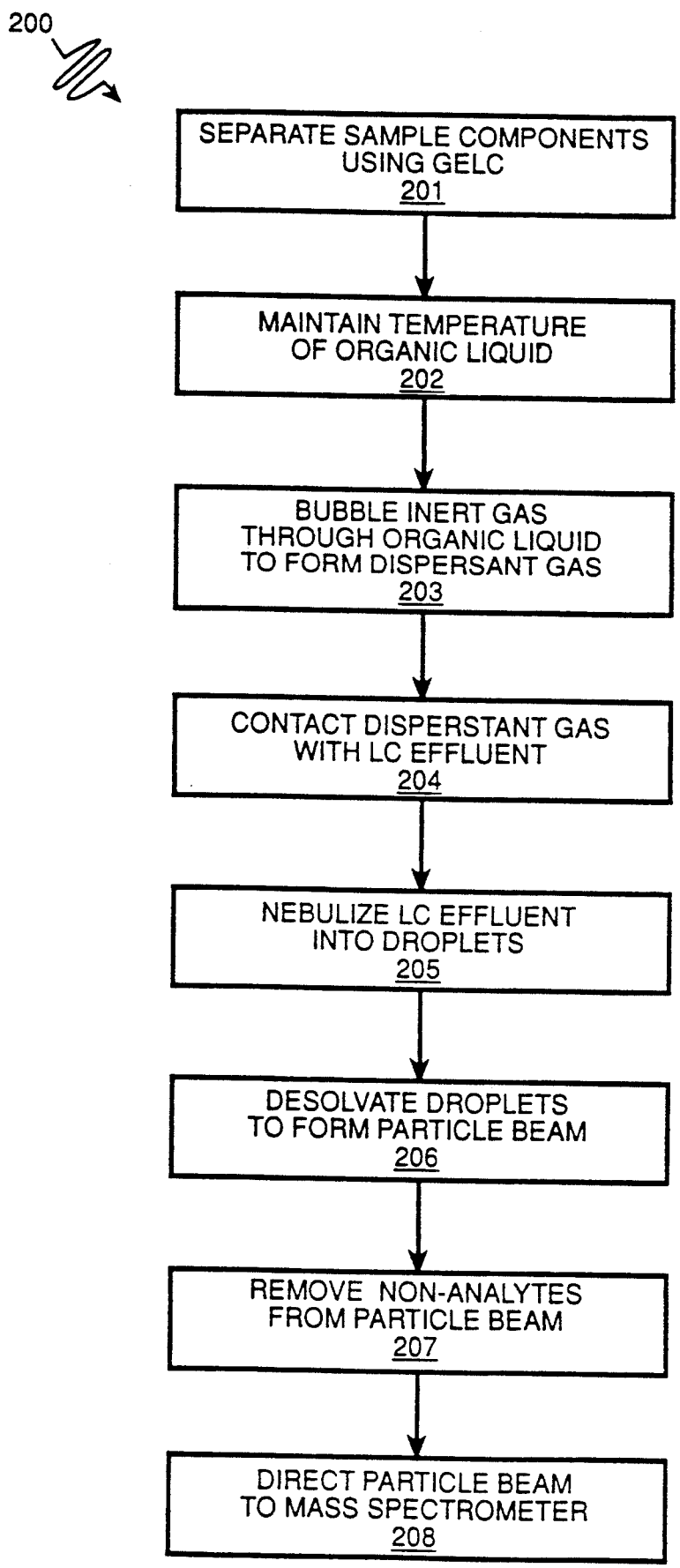
FIG. 2 is a flow chart of an LC/MS method incorporating a method of generating a particle beam in accordance with the present invention.

LC/MS system 100 provides for an enhanced method 200 for generating a particle beam, as flow-charted in FIG. 2. Method 200 begins with the reverse-phase gradient elution of a sample; the sample can have both polar and nonpolar component analytes. In a step 202, the temperature of the organic liquid is adjusted to and maintained below 20° C., preferably, between 0° C. and 8° C., for example, 4° C.

In a step 203, a steam of an inert gas, such as helium, is bubbled through the organic solvent so that at least some organic solvent vapor mixes with the inert gas, defining a dispersant gas (defined by its role during nebulization). Preferably, the distance traveled by the inert gas in the liquid solvent is sufficient so that the inert gas becomes substantially saturated with organic vapor. Saturation occurs when the partial pressure of organic vapor in the bubbles is such that the amount of organic vapor in a bubble condensing into liquid is substantially equal to the amount of liquid vaporizing into a bubble.

In a step 204, the dispersant gas contacts a solution of an analyte in a solvent. In the context of LC/MS system 100, this solution is the effluent of the liquid chromatographic column. At the later stages of a reverse-phase gradient elution, the solvent is predominantly water. In a step 205, the solution is nebulized into droplets. In a step 206, the droplets are desolvated, i.e., the solvent is vaporized and the droplets form an analyte particle beam. In a step 207, non-analytes, e.g., the inert gas, the organic vapor, and the solvent vapor, are removed from the analyte particle beam. In LC/MS system 100, the particle beam is directed to the ion source of the mass spectrometer to provide for mass filtering and detection.

While in the preferred method, LC/MS system 100 is operated in a reverse-phase gradient mode, the present invention provides for "forward" phase gradient elution and isocratic elution. Furthermore, the solvent need not be aqueous. The present invention provides advantages in desolvation with other solvents having a lower volatility than the organic material used as vapor in the dispersant gas.

Other than as described above, the preferred embodiment corresponds to the Hewlett-Packard LC/MS System 5988A with HP particle beam interface. This commercially distributed system is described in Publication No. 23-5956-4133, published by Hewlett-Packard Company, June, 1988. While the tests establishing the advantages of the present invention were performed in a modification of the LC/MS system described therein, the present invention also provides advantages for comparable LC/MS systems.

In particular, while in the preferred embodiment, the fluid and the dispersant gas enter a nebulizer through a common nebulizer port, the present invention also provides that the dispersant gas can enter through a different port than the liquid bearing the analyte. For example, the gas flow can intersect an analyte liquid jet at right angles.

Those skilled in the art can recognize that the advantages of the present invention are not limited by the source of the particle-beam generator input nor to the purpose to which the particle beam is used. Accordingly, the present invention provides for systems in which the liquid input to the particle-beam generator arrives from a source other than a liquid chromatography system; for example, the output can be the product of an Edmund degradation. Likewise, the present invention provides for applications where the output of the particle-beam generator is not provided to a mass spectrometer. For example, the output can be directed to an ion trap or be used to bombard a target. These and other modifications to and variations upon the preferred embodiments are provided for by the present invention, the scope of which is limited only by the following claims.

What is claimed is:

1. A particle-beam generator for generating a particle beam from a liquid solution including an analyte and a solvent liquid in which said analyte is dissolved, said particle-beam generator comprising:
   a carrier gas source for providing a carrier gas;
   mixing means for mixing said carrier gas with an organic vapor to provide a dispersant gas, said organic vapor being soluble in said solvent liquid, said mixing means being coupled to said carrier gas source;
   nebulizer means for nebulizing said solution into droplets, said nebulizer means being coupled to said mixing means for receiving said dispersant gas, said nebulizer means providing for contact between said dispersant gas and said solution;
   a desolvation chamber providing for vaporization of said solvent liquid to produce a solvent vapor; and
   a momentum separator for separating said analyte from said carrier gas, said organic vapor, and said solvent vapor to yield a particle beam of said analyte.

2. A particle-beam generator as recited in claim 1 wherein said mixing means includes a bubbler, said bubbler containing an organic liquid for providing said organic vapor.

3. A particle-beam generator as recited in claim 2 further comprising temperature control means for maintaining said organic solvent in said bubbler below 20° C.

4. A particle-beam generator as recited in claim 3 wherein said temperature control means maintains the temperature of said organic solvent between 0° C. and 8° C.

5. A particle-beam generator as recited in claim 1 wherein said nebulizer means includes conduit means for conveying said dispersant gas so that it contacts said solution before said solution is nebulized into droplets.

6. A liquid chromatography and mass spectrometry system comprising:
   a gradient-elution liquid chromatography subsystem for providing an effluent containing at least one analyte in a predominantly aqueous solvent;
   a helium source for providing helium;
   a bubbler containing a water-soluble organic liquid, said bubbler being coupled to said helium source for receiving helium therefrom, said bubbler providing a dispersant gas including said helium and organic vapor, said organic vapor arising from said organic liquid;
   temperature control means for maintaining said organic liquid between 0° C. and 8° C.;
   a nebulizer, said nebulizer being coupled to said analyte source for receiving said effluent, said nebulizer being coupled to said bubbler for receiving said disperant gas, said nebulizer providing for interaction between said gaseous mixture and said effluent so as to promote nebulization of said effluent;

a desolvation chamber providing for vaporization of said solvent to produce a solvent vapor;

a momentum separator for separating said analyte from said helium, said organic vapor and said solvent vapor to yield a particle beam of said analyte; and a mass spectrometer for providing a mass spectrum of said analyte, said mass spectrometer being coupled to said momentum separator for receiving said particle beam therefrom.

7. A method of generating a particle beam, said method comprising:

mixing an organic vapor with a carrier gas to provide a dispersant gas, said organic vapor being soluble in a solvent;

contacting a solution including said solvent and an analyte with said dispersant gas within a nebulizer so that said solution is nebulized;

vaporizing said solvent to produce solvent vapor; and separating said solvent vapor and said gaseous mixture from said analyte to yield a particle beam constituted by said analyte.

8. A method as recited in claim 7 wherein said mixing step involves bubbling a carrier gas through an organic liquid to provide said dispersant gas.

9. A method as recited in claim 8 wherein said organic liquid is maintained at a temperature between 0° and 8° C. during said bubbling.

10. An analytical method comprising:

separating component analytes of a sample mixture using gradientelution liquid chromatography so that a resulting effluent contains at least one analyte in a predominantly aqueous solvent;

maintaining a water-soluble organic liquid between 0° C. and 8° C.;

bubbling helium through said organic liquid to provide a dispersant gas including both helium and organic vapor;

contacting said effluent with said dispersant gas;

nebulizing said effluent so that said effluent breaks up into droplets including said analyte;

desolvating said droplets to yield an analyte particle beam and a solvent vapor;

separating said helium, said organic vapor, and said solvent vapor from said particle beam; and directing said particle beam to a mass spectrometer to obtain a mass spectrum of said analyte.

* * * * *